United States Patent [19]

Narisada et al.

[11] Patent Number: 4,504,658
[45] Date of Patent: Mar. 12, 1985

[54] EPIMERIZATION OF MALONIC ACID ESTERS

[75] Inventors: Masayuki Narisada, Osaka; Hiroshi Onoue; Mitsuaki Ohtani, both of Nara; Fumihiko Watanabe, Osaka, all of Japan

[73] Assignee: Shionogi & Co., Ltd., Osaka, Japan

[21] Appl. No.: 504,287

[22] Filed: Jun. 14, 1983

[30] Foreign Application Priority Data

Jul. 2, 1982 [JP] Japan .................. 57/116048

[51] Int. Cl.³ .......................... C07D 498/04
[52] U.S. Cl. .................................... 544/90
[58] Field of Search .......................... 544/90

[56] References Cited

U.S. PATENT DOCUMENTS

| 3,719,667 | 3/1973 | Gutowski .................. 260/239.1 |
| 4,138,486 | 2/1979 | Narisada et al. ........... 424/248.52 |
| 4,167,630 | 9/1979 | Firestone ................... 544/90 |
| 4,234,596 | 11/1980 | Christensen et al. ...... 544/90 X |
| 4,320,055 | 3/1982 | Blaszczak ................. 544/90 X |
| 4,323,567 | 4/1982 | Narisada et al. .......... 544/90 X |

*Primary Examiner*—Richard L. Raymond
*Attorney, Agent, or Firm*—Wenderoth, Lind & Ponack

[57] ABSTRACT

A compound represented by the formula (II) epimerizes by the action of a base and the product is precipitated for shifting the equilibrium to yield the corresponding epimer represented by the formula (I).

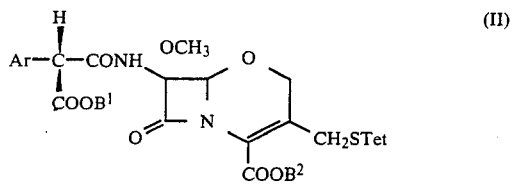

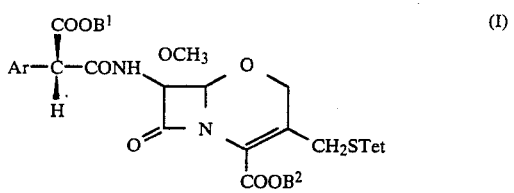

wherein
Ar is an optionally substituted aryl or heterocyclic group;
Tet is an optionally substituted tetrazolyl group and
$B^1$ and $B^2$ are each ester forming group in the field of penicillin or cephalosporin chemistry.

7 Claims, No Drawings

EPIMERIZATION OF MALONIC ACID ESTERS

INTRODUCTION

This invention relates to a process for preparing an epimer of a 7β-malonamido-7α-methoxy-3-tetrazolylthiomethyl-1-dethia-1-oxa-3-cephem-4-carboxylic acid ester represented by the formula (I) which comprises epimerizing the other corresponding epimer represented by the formula (II) with a base and then precipitating the product.

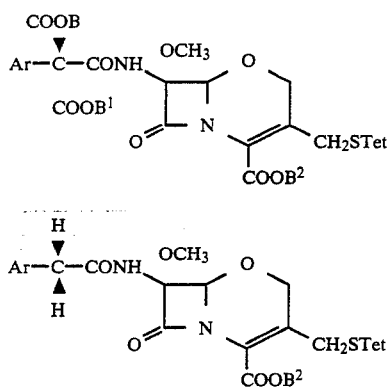

wherein
Ar is an optionally substituted aryl or heterocyclic group;
Tet is an optionally substitued tetrazolyl group and
$B^1$ and $B^2$ are each ester forming group in the field of penicillin or cephalosporin chemistry.

COMPOUNDS

The Ar group is a monocyclic or dicyclic and 5-membered or 6-membered ring aryl group or can be a heteroring group having a nitrogen, oxygen and/or sulfur atom in its skeleton. The Ar group is optionally substituted by e.g. halogen, hydroxy, $C_1$ to $C_3$ alkyl, alkoxy, alkanoyloxy or the like.

Here, representative heterocyclic groups are pyrrolyl, furyl, thienyl, pyrazolyl, imidazolyl, oxazolyl, thiazolyl, isothiazolyl, oxadiazolyl, thiadiazolyl, tetrazolyl, triazolyl, oxatriazolyl, thiatriazolyl, pyridyl, pyrimidyl, pyrazinyl, pyridazinyl, triazinyl, indolyl and the like.

More preferable Ar group can be phenyl, hydroxyphenyl, protected hydroxyphenyl, thienyl or the like, in which the protecting group can be, for example, alkanoyl, methoxyethyl, tetrahydropyranyl, p-methoxybenzyl, t-butyl or the like.

The substituent of the tetrazolyl group represented by Tet is preferably $C_1$ to $C_4$ alkyl to $C_1$ to $C_4$-alkyl further substituted by carboxy, esterified carboxy, cyano, dimethylamino or the like.

The carboxy protecting group $B^1$ or $B^2$ can be that well known in the field of penicillin or cephalosporin chemistry as capable of being introduced or deprotected under a condition without adverse effect on other parts of the molecule.

Illustrative of the protecting groups are those wherein $B^1$ and $B^2$ each is the same or different $C_1$ to $C_6$-alkyl or $C_7$ to $C_{12}$-aralkyl optionally substituted by halogen, $C_1$ to $C_3$-alkoxy or nitro.

Such a protective group can be that forming an optionally substituted aliphatic ester, e.g., t-butyl, trichloroethyl, allyl or the like ester, especially 1-oxyalkyl ester as 1-alkanoyloxyalkyl ester, e.g., acetoxymethyl, pivaloyloxymethyl or the like ester, 1-alkoxyformyloxyalkyl ester, e.g., ethoxycarbonyloxyethyl or like ester, 1-alkoxyaliphatic ester, e.g., methoxymethyl, tetrahydropyranyl, 2-oxo-1,3-dioxolenylmethyl or like ester, aralkyl ester, e.g., benzyl, methylbenzyl, dimethylbenzyl, methoxybenzyl, ethoxybenzyl, nitrobenzyl, aminobenzyl, diphenylmethyl, phthalidyl, phenacyl or like ester, aryl ester, e.g., phenyl, tolyl, xylyl, pentachlorophenyl, indanyl or like ester, or other types of ester forming group.

The protective group is usually absent in the target antibacterial compound. Thus, the structure of the protective group in itself has less importance so long as the objective carboxy protection is satisfactory and it is accompanied with less side reactions and does not affect the course of the reaction.

BACKGROUND OF INVENTION

The compounds represented by the formula (I) are useful as intermediates for preparing antibacterials represented by the formula (I) but in which $B^1$ and/or $B^2$ are a hydrogen or alkali metal atom, e.g., latamoxef or its salt, i.e., $B^1$ and $B^2$ are hydrogen or sodium, Ar is hydroxyphenyl and Tet is 1-methyl-1H-tetrazol-5-yl or its derivatives.

When the compound (I) is prepared by chemical synthesis, it is a mixture of (S)- and (R) epimers (I) and (II), and hardly purified by mere crystallization. Then, for preparing the desired antibacterial substance in highly pure state or for storing the intermediate for a long time in a stable form, it is necessary to separate each epimers and then to purify each stereoisomer separately. There has been used a tedious chromatography for this separation, but this method was unsuitable for a large scale production.

The present inventors sought a method for separating these epimers on an industrial scale and found that when a compound represented by the formula (II) is dissolved in ethyl acetate and concentrated in the presence of pyridine to show over 80% of the epimer (II) isomerized to the corresponding epimer (I) and then crystallized as the pure epimer (I). This invention is completed based on this discovery.

UNOBVIOUSNESS, EFFECT AND USE OF THIS INVENTION

It is known that said latamoxef isomerizes from the (s)-epimer (I) to the corresponding (R)-epimer (II) when it is in sodium or ammonium salt form. The fact that the synthetic intermediate of latamoxef in an ester form, i.e., Compound (I), goes in another direction, i.e., from (R)-epimer (II) to (S)-epimer (I) was quite unexpectable.

By using the epimerization of this invention, one can obtain a highly pure epimer suitable for storage for a long time for producing highly pure end products.

Generally, latamoxef or a closely related antibacterial has higher antibacterial activity when it is the (R)-epimer (II) than when it is the (S)-epimer (I). However, the compound (I) of this invention epimerizes from its (S)- to antibacterially favourable (R)-configuration during the reactions and work up to make the objective latamoxef (II) where $B^1$ and $B^2$ are hydrogens. Thus, one can avoid any trouble arising from the fact that the compound of this invention is the stereochemically reversal epimer.

PROCESS OF THIS INVENTION

The process of this invention is carried out by dissolving a compound represented by the formula (II) in a solvent, mixed with a base, and then precipitating the epimer by standing for a while, by diluting with a difficultly dissolving solvent or by concentrating. For the epimerization of this invention, the precipitate may be not always in a crystalline form.

Illustrative of the base to be employed in the epimerization are alkali metal hydrogen carbonate, tri-lower alkylamine, diethanolamine, triethanolamine, pyridine, picoline, lutidine or collidine.

The solvent can be water or an organic solvent, e.g., an industrial organic solvent belonging to a series of hydrocarbon, e.g., pentane, hexane, octane, benzene, toluene or xylene; halohydrocarbon, e.g., dichloromethane, chloroform, carbon tetrachloride, dichloroethane, trichloroethane or chlorobenzene; ether, e.g., diethyl ether, methyl isopropyl ether, dioxane or tetrahydrofuran, ketone, e.g., acetone, methyl ethyl ketone or cyclohexanone; ester, e.g., ethyl acetate, isobutyl acetate, methyl benzoate or isopropyl benzoate; nitrohydrocarbon, e.g., nitromethane or nitrobenzene; nitrile, e.g., acetonitrile or benzonitrile; amide, e.g., formamide, acetamide, dimethylformamide, dimethylacetamide or hexamethylphosphorotriamide; sulfoxide, e.g., dimethyl sulfoxide or thiane-1,1-dioxide; organic base, e.g., diethylamine, triethylamine, diethanolamine, pyridine, picoline, collidine or quinoline; or alcohol, e.g., methanol, ethanol, propanol, hexanol, octanol or benzyl alcohol; or an industrial solvent belonging to other series of solvents or mixtures of two or more of above cited solvents. Especially preferable is a hydrocarbon, halohydrocarbon, ester, ketone, ether, alcohol, amide or sulfoxide solvent or water.

The amount of the base to be added can be from 100 ppm to several percent. The amount of the solvent is usually the amount capable of dissolving the starting material or more, and the reaction temperature is usually in a range of from $-50°$ C. to 100° C. The difficulty dissolving solvent can be one selected from the above solvents which dissolves the objective compound (II) sparingly. For concentrating ther is usually used vacuum evaporation. When the product is amorphous, the concentrating rate is carefully controlled so as not to separate the unreacted starting epimer (II).

As stated before, the product of this invention is useful as the starting material for synthesizing antibacterial β-lactams.

EXAMPLES

The following examples illustrate the embodiments of this invention. The abbreviations used in the examples are commonly in use by those skilled in the art.

EXAMPLE 1

(1) To a solution cooled at 0° C. of 7β-(α-p-hydroxyphenylmalonamido)-7α-methoxy-3-(1-methyl-5-tetrazolyl)thiomethyl-1-dethia-1-oxa-3-cephem-4-carboxylic acid (5.20 g) in methanol (50 ml) is added dropwise dichloromethane (93 ml) containing 5% diphenyldiazomethane. After 1 hour's stirring under ice cooling, the solution is concentrated under reduced pressure. The resultant material is purified by silica gel chromatography to give the corresponding bisdiphenylmethyl ester (8.5 g) from the fractions eluted with benzene-ethyl acetate (2:1) mixture. This product is a mixture (1:1) of the (R)- and (S)-epimers at the α-position of the side chain attached to the 7-position.

A part of the product (3.0 g) is dissolved in a mixture of ethyl acetate (20 ml) and pyridine (0.1 ml) and let stand at room temperature for a day. The separated crystals are collected by filtration to obtain the objective (S)-epimer (4.45 g). Yield: 75%. The product contains 2 molar equivalents of crystal ethyl acetate. mp. 119°–122° C.

NMR (CD$_3$COCD$_3$) δ: 1.18 (t, J=7 Hz, 6H), 1.92 (s, 6H), 3.37 (s, 3H), 3.88 (s, 3H), 4.05 (q, J=7 Hz, 4H), 4.30 (s, 2H), 4.60 (s, 2H), 4.97 (s, 1H), 5.12 (s, 1H), 6.72+6.85s (A-part of Ab quartet, J=8 Hz, 2H), 6.85 (s, 1H), 6.92 (s, 1H), 7.1–7.9 (m, 23H).

(2) By crystallizing (R)-epimer or (S)-epimer (3.0 g) from benzene (30 ml) containing pyridine (0.1 ml), one obtains the same (S)-epimer (ca. 2.5 g). Yield: 73%. This product contains 1.5 molar equivalent of crystal benzene. mp. 119°–122° C.

NMR (CD$_3$COCD$_3$) δ: 3.37 (s, 3H), 3.88 (s, 3H), 4.30 (s, 2H), 4.60 (s, 2H), 4.97 (s, 1H), 5.12 (s, 1H), 6.72s+6.85s (A-part of AB quartet, J=8 Hz, 2H), 6.85 (s, 1H), 6.92 (s, 1H), 7.1–7.9 (m, 32H).

EXAMPLE 2

By reacting 7β-(α-p-hydroxyphenylmalonamido)-7α-methoxy-3-(1-methyl-5-tetrazolyl)thiomethyl-1-dethia-1-oxa-3-cephem-4-carboxylic acid with p-nitrophenyldiazomethane prepared from p-nitrobenzalhydrazine by oxidizing with nickel peroxide, the corresponding bis-p-nitrobenzylester (a mixture of (R)- and (S)-epimers) can be obtained. This mixture is crystallized from dichloromethane containing lutidine to afford the (S)-epimer. mp. 120°–123° C.

The same product can be prepared by treating the same starting material in the form of the disodium salt with a molar equivalent amount of p-nitrobenzyl bromide in N,N-dimethylacetamide for 1.5 hours, and then crystallizing the product from dichloromethane containing 0.1% quinoline. mp. 120°–123° C.

NMR (CD$_3$COCD$_3$) δ: 3.33 (s, 3H), 3.92 (s, 3H), 415s+4.45s (A-part of ABq, J=14 Hz, 2H), 4.62 (s, 2H), 4.95 (s, 1H), 5.08 (s, 1H), 5.18s+5.47s (A-part of ABq, J=14 Hz, 2H), 5.45(s, 2H), 6.82s+7.32s (A-part of ABq, J=5 Hz, 4H), 7.57–8.32 (m, 10H).

EXAMPLE 3

To a solution of p-methoxybenzyl iodide prepared from p-methoxybenzyl chloride (37.59 g) and sodium iodide (35.97 g) in dimethylformamide (300 ml) at 0° C. for 1 hour are added 7β-(α-(RS)-hydroxyphenylmalonamido)-7α-methoxy-3-(1-methyl-5-tetrazolyl)thiomethyl-1-dethia-1-oxa-3-cephem-4-carboxylic acid disodium salt (33.87 g) and triethylamine (4.16 ml). After stirring at room temperature for 2 hours, the mixture is diluted with ethyl acetate, washed with diluted hydrochloric acid and water, dried over sodium sulfate and concentrated to dryness under reduced pressure. The residue is dissolved in a mixture of benene and ethyl acetate (1:1) and passed through a layer of silica gel. The solution is concentrated to dryness and the resultant solid is dissolved in dichloromethane containing triethylamine and diluted with benzene to separate crystals which are collected by filtration and washed with benzene to give the corresponding bis-p-methoxybenzyl ester (S)-epimer (34 g). mp. 95°–97° C.

Yield: 74%.

IR (CHCl$_3$) $\nu$: 3600, 3410, 3328, 1786, 1719, 1695 cm$^{-1}$.

NMR (CD$_3$COCD$_3$) δ: 3.28 (s, 3H), 3.77 (s, 6H), 3.94 (s, 3H), 4.13d+4.40d (ABq, J=13.5 Hz, 2H), 4.78 (s, 1H), 5.00 (s, 1H), 5.07 (s, 2H), 5.21 (s, 2H), 6.67-7.48 (m, 12H), 8.05 (s, 1H), 8.26 (s, 1H).

EXAMPLE 4

A solution of 7β-amino-7α-methoxy-3-(1-methyl-5-tetrazolyl)thiomethyl-1-dethia-1-oxa-3-cephem-4-carboxylic acid diphenylmethyl ester (107 mg), pyridine (70 μl), p-tetrahydropyranyloxyphenylmalonic acid mono-p-methoxybenzyl ester (84 mg) and phosphorus oxychloride (20 μl) in dichloromethane (1 ml) cooled at −5° C. is stirred for 30 minutes and mixed with aqueous 5% sodium hydrogen carbonate (70 μl). After evaporating dichloromethane under reduced pressure, the residual solution is extracted with ethyl acetate. The extract is washed with 2N-hydrochloric acid and water, dried over sodium sulfate and concentrated under reduced pressure. The residue is dissolved in acetone, cooled at 0° C., acidified with concentrated hydrochloric acid (3 drops) and stirred for 45 minutes. The reaction mixture is made basic with aqueous 5% sodium hydrogen carbonate (0.9 ml) and stirred for 1 hour. The solution is diluted with water to separate precipitate. This is collected by filtration, washed with a mixture of acetone and water (1:1) and water and dried to give 7β-(α-p-methoxybenzyloxycarbonyl-p-hydroxyphenylacetamido)-7α-methoxy-3-(1-methyl-5-tetrazolyl)thiomethyl-1-dethia-1-oxa-3-cephem-4-carboxylic acid diphenylmethyl ester (S)-epimer (102 mg).

NMR (CD$_3$COCD$_3$) δ: 3.23 (s, 3H), 3.72 (s, 3H), 3.87 (s, 3H), 4.23 (s, 2H), 4.53 (s, 2H), 4.83 (s, 1H), 5.03 (s, 2H), 5.13 (s, 1H), 6.73 (A-part of A$_2$B$_2$, J=9 Hz, 2H), 6.87 (s, 1H), 6.88 (A-part of A$_2$B$_2$, J=9 Hz, 2H), 7.13-7.67 (m, 14H), 9.30 (s, 1H).

This precipitate is crystallized from ethyl acetate and dried for 7 hours under a stream of air to give crystals of monohydrate. mp. 142°-144° C.

NMR (CD$_3$COCD$_3$) δ: 3.38 (s, 3H), 3.80 (s, 3H), 3.93 (s, 3H), 4.32 (s, 2H), 4.63 (s, 2H), 4.83 (s, 1H), 5.11 (s, 3H), 6.73s+6.87s (A-part of ABq, J=8 Hz, 2H), 6.83s+6.96s (A-part of ABq, J=8 Hz, 2H), 6.92 (s, 1H), 7.19-7.79 (m, 21H), X-ray spectrum (Cu: N$_1$, 40 KV, 20 mA, λ=1.5405) 2θ: 6.1w, 8.5m, 10.1m, 10.1m, 10.6m, 11.5w, 12.2m, 14.3s, 15.1m, 15.5s, 16.9m, 18.3vs, 19.6m, 20.6vs, 21.5w, 22.7vs, 23.7w, 25.0m, 26.6w, 27.4w, 27.8w, 29.1m, 30.8w, 31.8w, 33.1w, 33.1w, 33.9w, 34.6vw, 35.4w, 36.0vw, 36.3vw, 37.1vw.

EXAMPLE 5

Under a reaction condition similar to that of Example 4, 7β-amino-7α-methoxy-3-(1-methyl-5-tetrazolyl)thiomethyl-1-dethia-1-oxa-3-cephem-4-carboxylic acid diphenylmethyl ester and (RS)-α-diphenylmethoxycarbonyl-p-tetrahydropyranyloxyphenylacetyl chloride give 7β-(α-diphenylmethoxycarbonyl-p-tetrahydropyranyloxyphenylacetamido)-7α-methoxy-3-(1-methyl-5-tetrazolyl)thiomethyl-1-dethia-1-oxa-3-cephem-4-carboxyic acid diphenylmethyl ester (a mixture of (R)- and (S)-epimers), which is hydrolyzed with hydrochloric acid and crystallized from a mixture of benzene and pyridine to afford 7β-(α-diphenylmethoxycarbonyl-p-hydroxyphenylacetamido)-7α-methoxy-3-(1-methyl-5-tetrazolyl)thiomethyl-1-dethia-1-oxa-3-cephem-4-carboxylic acid diphenylmethyl ester (S)-epimer.

This product is the same as that of Example 1.

EXAMPLE 6

Under a reaction condition similar to that of Example 4, 7β-amino-7α-methoxy-3-(1-methyl-5-tetrazolyl)thiomethyl-1-dethia-1-oxa-3-cephem-4-carboxylic acid diphenylmethyl ester and (RS)-α-p-methoxybenzyloxycarbonyl-p-hydroxyphenylacetyl chloride give 7β-(2-p-hydroxyphenyl-2-p-methoxybenzyloxycarbonylacetamido)-7α-methoxy-3-(1-methyl-5-tetrazolyl)thiomethyl-1-dethia-1-oxa-3-cephem-4-carboxylic acid diphenylmethyl ester (a mixture of (R)- and (S)-epimers). This is recrystallized from a mixture of ethyl acetate and diethanolamine to give the (S)-epimer in 90% yield.

The product is the same as that of Example 4.

EXAMPLE 7

Crystallization of 7β-(2-p-hydroxyphenyl-2-(5-indanyl)oxycarbonylacetamido)-7α-methoxy-3-(1-methyl-5-tetrazolyl)thiomethyl-1-dethia-1-oxa-3-cephem-4-carboxylic acid diphenylmethyl ester (a mixture of (R)- and (S)-epimers, 230 mg) from a mixture of chloroform and ether containing 0.05% diethanolamine gives the (S)-epimer (88 mg). mp. 114°-116° C.

IR (CHCl$_3$) $\nu$: 3590, 3335, 1789, 1736, 1722, 1700, 1601 cm$^{-1}$.

NMR (CD$_3$COCD$_3$) δ: 2.1 (m, 2H), 2.87 (t, J=7 Hz, 4H), 3.43 (s, 3H), 3.91 (s, 3H), 4.31 (s, 2H), 4.65 (s, 2H), 5.07 (s, 1H), 5.13 (s, 1H), 6.92 (brs, 3H), 6.8-7.7 (m, 16H), 8.25 (m, 1H).

EXAMPLE 8

(1) To a stirred solution of 7β-benzamido-7α-methoxy-3-(1-methyl-5-tetrazolyl)thiomethyl-1-dethia-1-oxa-3-cephem-4-carboxylic acid diphenylmethyl ester (6.13 g) in dichloromethane (50 ml) are added pyridine (1.77 ml) and phosphorus pentachloride (4.2 g), and the mixture is refluxed for 1 hour under nitrogen. The reaction mixture is cooled at −15° C. to −10° C., diluted with methanol (200 ml), and stirred for 3 hours at 0° C. The reaction mixture is stirred for 15 minutes on admixture with diethylamine (8.28 ml). The reaction mixture then is diluted with dichloromethane, washed with water, dried and concentrated. The residue is diluted with ether to crystallize 7β-amino-7α-methoxy-3-(1-methyl-5-tetrazolyl)thiomethyl-1-dethia-1-oxa-3-cephem-4-carboxylic acid diphenylmethyl ester (3.97 g). mp. 160°-162° C. (decomp.).

(2) To a solution of the product of above (1) (1.02 g), pyridine (0.7 ml) and 2-(p-(p-methoxybenzyl)oxyphenyl)-2-p-methoxybenzyloxycarbonylacetic acid (1.0 g) in dichloromethane is added phosphorus oxychloride (0.2 ml) under stirring at −12° C., and the mixture is stirred for 30 minutes at −5° C. This is neutralized with aqueous 5% sodium hydrogen carbonate (7 ml), concentrated and extracted with ethyl acetate. The extract is washed with 2N-hydrochloric acid and water, dried over sodium sulfate and concentrated. The resultant mixture of (R)- (S)-epimers is crystallized from benzene containing 0.1% picoline to give 7β-(2-p-(p-methoxybenzyloxy)phenyl-2-p-methoxybenzyloxycarbonylacetamido)-7α-methoxy-3-(1-methyl-5-tetrazolyl)thiomethyl-1-dethia-1-oxa-3-cephem-4-carboxylic acid diphenylmethyl ester (S)-epimer (1.6 g).

IR (CHCl$_3$) $\nu$: 1792, 1725, 1700 cm$^{-1}$.

NMR (CDCl$_3$) δ: 3.45 (s, 3H), 3.78 (s, 6H), 3.82 (s, 3H), 4.27 (brs, 2H), 4.57 (brs, 3H), 4.98 (s, 2H), 5.03 (s, 1H), 5.13 (s, 2H).

EXAMPLE 9

A solution of 7β-(2-diphenylmethoxycarbonyl-2-(3-thienyl)-acetamido)-7α-methoxy-3-(1-methyl-5-tetrazolyl)thiomethyl-1-dethia-1-oxa-3-cephem-4-carboxylic acid diphenylmethyl ester in benzene containing 0.1% pyridine (3 parts by weight) is kept under ice cooling for 2 hours and at room temperature for 5 hours to separate crystals which are collected by filtration to afford the corresponding (S)-epimer in 43% yield. This contains ⅓ molar equivalents of crystal benzene. mp. 85°–92° C.

IR (CHCl$_3$) ν: 3405, 3330, 1790, 1723, 1704, 1633, 1602, 1587, 1498, 1166 cm$^{-1}$.

NMR (CD$_3$COCD$_3$) δ: 3.43 (s, 3H), 3.83 (s, 3H), 4.23 (s, 2H), 4.53 (s, 2H), 5.08 (s, 1H), 5.18 (s, 1H), 6.82 (s, 1H), 6.85 (s, 1H), 7.07–7.70 (m, 24H).

What we claim is:

1. A process for preparing a compound of the formula

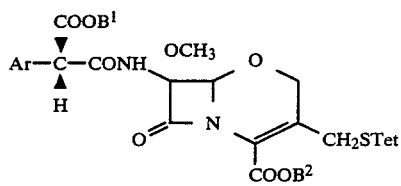

wherein Ar represents mono- or dicyclic aryl in which the cyclic groups are 5 or 6 membered or a heterocyclic group selected from pyrrolyl, furyl, thienyl, pyrazolyl, imidazolyl, oxazolyl, thiazolyl, isothiazolyl, oxadiazolyl, thiadiazolyl, tetrazolyl, triazolyl, oxatriazolyl, thiatriazolyl, pyridyl, pyrimidyl, pyrazinyl, pyridazinyl, triazinyl or indolyl, said aryl and heterocyclic groups being unsubstituted or substituted by halogen, hydroxy, C$_1$ to C$_3$ alkyl, alkoxy or alkanoyloxy, tet is tetrazolyl which is unsubstituted or substituted by C$_1$ to C$_4$ alkyl or C$_1$ to C$_4$ alkyl substituted by carboxy, esterified carboxy, cyano or dimethylamino, B$^1$ and B$^2$ independently represent a carboxy protecting group capable of being introduced into or removed from the molecule under conditions which do not have an adverse effect on the other portions of the molecule, which comprises subjecting a compound of the formula

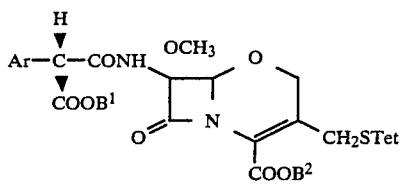

to epimerization with a base selected from the group consisting of alkali metal hydrogen carbonate, tri-lower alkylamine, diethanolamine, triethanolamine, pyridine, picoline, lutidine or collidine and subsequently precipitating the product.

2. A process as claimed in claim 1 wherein Ar is hydroxyphenyl or thienyl.

3. A process as claimed in claim 1 wherein B$^1$ and B$^2$ each is the same or different and is selected from t-butyl, p-methoxybenzyl and diphenylmethyl.

4. A process as claimed in claim 1 wherein the base is selected from the group consisting of sodium hydrogen carbonate, triethylamine and triethanolamine.

5. A process as claimed in claim 1 wherein the epimerization is effected in a solvent selected from the group consisting of benzene, dichloromethane, chloroform, ether, ethyl acetate, methanol, ethanol, acetone, water and a mixture thereof.

6. A process as claimed in claim 1 wherein the precipitation is effected by adding sparingly dissolving solvent, concentrating or crystallizing.

7. A process as claimed in claim 1 wherein the epimerization is effected at a temperature between −20° C. and 50° C. for a time between 5 minutes and 10 hours.

* * * * *